US009925319B2

United States Patent
Valiorgue et al.

(10) Patent No.: US 9,925,319 B2
(45) Date of Patent: Mar. 27, 2018

(54) METHODS AND APPARATUSES FOR IMPEDANCE-BASED GAS DETECTION FOR MICROFLUIDIC SYSTEMS

(71) Applicant: Purdue Research Foundation, West Lafayette, IN (US)

(72) Inventors: Pierre Valiorgue, West Lafayette, IN (US); Justin A. Weibel, West Lafayette, IN (US); Suresh V. Garimella, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 89 days.

(21) Appl. No.: 15/085,673

(22) Filed: Mar. 30, 2016

(65) Prior Publication Data

US 2016/0287772 A1    Oct. 6, 2016

Related U.S. Application Data

(60) Provisional application No. 62/142,053, filed on Apr. 2, 2015.

(51) Int. Cl.
*A61M 1/16* (2006.01)
*A61M 1/36* (2006.01)
*B01L 3/00* (2006.01)

(52) U.S. Cl.
CPC ............ *A61M 1/16* (2013.01); *A61M 1/3626* (2013.01); *B01L 3/5027* (2013.01);
(Continued)

(58) Field of Classification Search
CPC ........ A61M 1/3626; A61M 2205/0244; A61M 2205/3317; A61M 1/14; A61M 1/16;
(Continued)

(56) References Cited

U.S. PATENT DOCUMENTS 6,463,312 B1 * 10/2002 Bergveld ........... A61B 5/14528
                                                600/309
7,291,512 B2 * 11/2007 Unger ................... B01L 3/5025
                                                438/50

(Continued)

OTHER PUBLICATIONS

Kubáň, Pavel, and Peter C. Hauser. "Contactless conductivity detection for analytical techniques: developments from 2010 to 2012." Electrophoresis34.1 (2013): 55-69.*

(Continued)

*Primary Examiner* — Lisa Caputo
*Assistant Examiner* — Punam Roy
(74) *Attorney, Agent, or Firm* — Hartman Global IP Law; Gary M. Hartman; Domenica N.S. Hartman (57) ABSTRACT

Methods and apparatuses for detection of gas bubbles in a microchannel configured for a conductive fluid to flow therethrough. The methods and apparatuses utilize a plate and at least two aligned electrodes embedded within the plate. The plate is configured to be located over the microchannel such that the at least two aligned electrodes are located along a length of the microchannel in the flow direction. Impedance is measured between the electrodes, and the percentage of gas within the fluid flowing through the microchannel is measured based on the measured impedance between the electrodes.

11 Claims, 5 Drawing Sheets

(52) U.S. Cl.
CPC .............. *A61M 2205/0244* (2013.01); *A61M 2205/3317* (2013.01); *A61M 2205/702* (2013.01); *B01L 2300/0645* (2013.01); *B01L 2300/0816* (2013.01)

(58) Field of Classification Search
CPC ..... B01L 2300/0645; B01L 2300/0816; B01L 3/5027
See application file for complete search history.

(56) References Cited

U.S. PATENT DOCUMENTS

| | | | | |
|---|---|---|---|---|
| 8,016,798 | B2* | 9/2011 | Sparks | A61M 5/16827 604/246 |
| 8,128,822 | B2* | 3/2012 | Browning | A61M 1/16 210/321.71 |
| 8,408,073 | B2* | 4/2013 | Sparks | A61M 5/16831 73/861.355 |
| 9,228,977 | B2* | 1/2016 | Mahabadi | G01N 27/44791 |
| 2003/0167035 | A1* | 9/2003 | Flaherty | A61M 5/14248 604/67 |
| 2005/0046429 | A1* | 3/2005 | Gruebler | G01F 1/64 324/693 |
| 2006/0011493 | A1* | 1/2006 | Kontschieder | G01N 27/10 205/792 |
| 2006/0046300 | A1* | 3/2006 | Padmanabhan | B01L 3/5027 436/55 |
| 2006/0275907 | A1* | 12/2006 | Glocker | A61B 5/021 436/70 |
| 2007/0240986 | A1* | 10/2007 | Reymond | B01L 3/5027 204/412 |
| 2010/0326916 | A1* | 12/2010 | Wrazel | A61M 1/16 210/646 |
| 2011/0140721 | A1* | 6/2011 | Mahabadi | G01N 27/4473 324/688 |
| 2011/0155667 | A1* | 6/2011 | Charest | A61M 1/16 210/651 |
| 2012/0085648 | A1* | 4/2012 | Kartalov | A61M 1/3496 204/547 |
| 2012/0292246 | A1* | 11/2012 | Jovanovic | B01D 61/18 210/321.6 |

OTHER PUBLICATIONS

Zhao, Min, et al. "A Portable Fill- and-Flow Channel Biosensor with an Electrode to Predict the Effect of Interferences." Electroanalysis 16.15 (2004): 1221-1226.*

Valiorgue, Pierre, et al. "Design of a non-intrusive electrical impedance-based void fraction sensor for microchannel two-phase flows." Measurement Science and Technology 25.9 (2014): 095301.*

Wang, M., W. Yin, and N. Holliday. "A highly adaptive electrical impedance sensing system for flow measurement." Measurement Science and Technology 13.12 (2002): 1884.*

Canière, Hugo, et al. "Mapping of horizontal refrigerant two-phase flow patterns based on clustering of capacitive sensor signals." International Journal of Heat and Mass Transfer 53.23 (2010): 5298-5307.*

Gijsenbergh, Pieter, and Robert Puers. "Permittivity-based void fraction sensing for microfluidics." Sensors and Actuators A: Physical 195 (2013): 64-70.*

P. Andreussi, A. Di Donfrancesco, M. Messia, "An impedance method for the measurement of liquid hold-up in two-phase flow", In International Journal of Multiphase Flow, vol. 14, Issue 6, 1988, Abstract.*

Sidharth Paranjape, Susan N. Ritchey, Suresh V. Garimella, "Electrical impedance-based void fraction measurement and flow regime identification in microchannel flows under adiabatic conditions"; International Journal of Multiphase Flow; Feb. 15, 2012; 175-183.

\* cited by examiner

METHODS AND APPARATUSES FOR IMPEDANCE-BASED GAS DETECTION FOR MICROFLUIDIC SYSTEMS

CROSS REFERENCE TO RELATED APPLICATIONS

This application claims the benefit of U.S. Provisional Application No. 62/142,053, filed Apr. 2, 2015, the contents of which are incorporated herein by reference.

STATEMENT REGARDING FEDERALLY SPONSORED RESEARCH

This invention was made with government support under Contract No. N00014-10-1-0921 awarded by the U.S. Navy Office of Naval Research. The Government has certain rights in the invention.

BACKGROUND OF THE INVENTION

The present invention generally relates to fluidic devices. The invention particularly relates to fluidic devices equipped with microchannels and methods for detection of gas bubbles in a conductive fluid flowing through such a microchannel.

Fluidic microchannels are found in many biological systems and provide high rates of heat and mass transfer in organs such as the brain, lungs, liver and kidneys. The efficient heat transfer provided by small-scale channels is also exploited for high heat flux cooling applications.

A challenge encountered during the development of microchannel-based devices, as an example, for microchannel-based hemodialysis, is detection of gas bubbles in a microchannel that may disrupt fluid flow or cause other undesirable flow conditions within the device. Moreover for certain medical applications such as hemodialysis, there is critical need to detect and avoid bubbles in the blood to prevent air embolisms, which is a potentially fatal complication. Measurement of the gas void fraction in small-scale (micro) channels is essential for predicting two-phase flow, heat transfer, and pressure drop.

Gas void fraction detection has been widely investigated at the macro-scale. When optical access is available, direct visualization is usually performed to detect gas voids. A variety of alternative methods such as radiation, ultrasound, and electrical impedance-based void fraction sensing methods have been developed to enable real-time measurement without optical access. Electrical impedance-based methods, which are well suited for gas void fraction detection in blood and other conductive liquids, encompass three primary implementation approaches: intrusive wire mesh sensors that detect phase (liquid or gas) at discrete locations on a grid over the flow cross-section, non-intrusive electrode-pair sensors flush-mounted in a pipe wall, and impedance tomography sensors that use sets of circumferential electrodes. Electrode configurations generally include helical electrodes wound around the channel, opposing crosswise electrodes, and electrodes placed along the channel length. Recent studies have reported the investigation of crosswise electrode void fraction sensors for medical applications (e.g., hemodialysis), one at the macroscale and one at the microscale level (e.g., dimensions of up to 100 micrometers).

Figure 1:
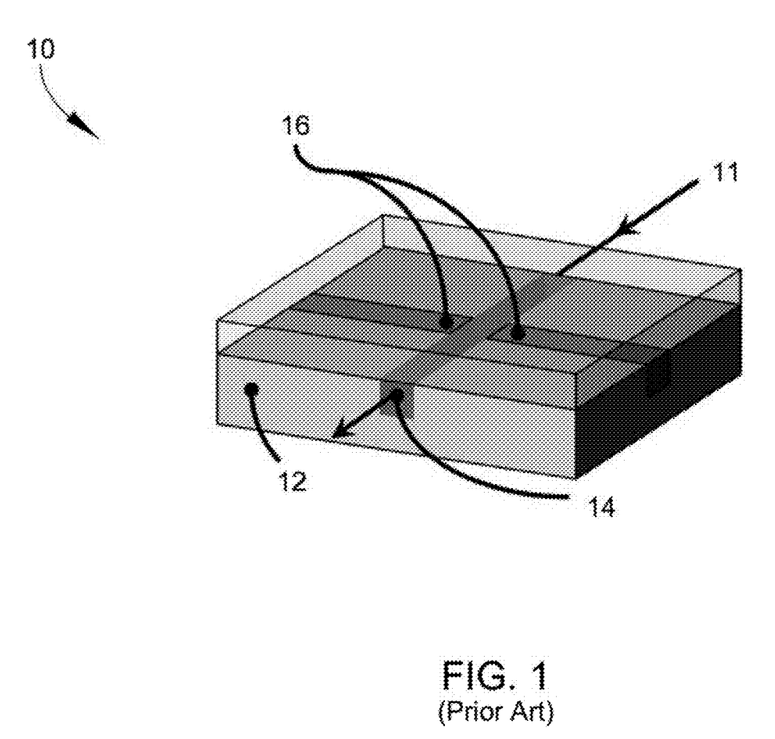
FIG. 1 schematically represents a nonlimiting electrical impedance-based sensor having a crosswise electrode pair configuration.

FIG. 1 represents what is herein referred to as "crosswise" sensor 10. Such sensors are described in Valiorgue et al., *Design of a non-intrusice electrical impedance-based void fraction sensor for microchannel two-phase flows*, Meas. Sci. Technol., 25(9):095301 (July 2014), incorporated herein by reference. The crosswise sensor 10 includes electrodes 16 on oppositely-disposed sides of a microchannel 14 formed in a substrate 12. Impedance is measured across the microchannel 14 between the electrodes 16 as a fluid flows in a flow direction 11 through the microchannel 14. While effective for detecting gas bubble in microchannels carrying a conductive fluid, such sensors may be difficult or impractical to implement in systems comprising an array of closely spaced microchannels.

In view of the above, there is a continuing desire for methods and apparatuses suitable for detection of gas bubbles in microchannels carrying a conductive fluid.

BRIEF DESCRIPTION OF THE INVENTION

The present invention provides methods and apparatuses suitable for detection of gas bubbles in microchannels carrying a conductive fluid, a nonlimiting example being the detection of gas bubbles in blood during a hemodialysis treatment of a patient.

According to one aspect of the invention, an apparatus is provided for detection of gas bubbles in a conductive fluid flowing through a microchannel formed in a substrate. The apparatus includes a plate and at least two aligned electrodes embedded within the plate. The plate is configured to be located over the microchannel such that the at least two aligned electrodes are located along a length of the microchannel in a flow direction of the conductive fluid flowing through the microchannel. The apparatus further includes means for measuring an impedance between the electrodes, and means for determining a percentage of gas in the conductive fluid flowing through the microchannel based on the measured impedance between the electrodes.

According to another aspect of the invention, a method is provided for detection of gas bubbles in a conductive fluid flowing through a microchannel formed in a substrate. The method includes providing a plate having at least two aligned electrodes embedded within the plate, locating the plate over the microchannel such that the at least two aligned electrodes are located along a length of the microchannel in the flow direction, measuring an impedance between the electrodes, and determining a percentage of gas in the conductive fluid flowing through the microchannel based on the measured impedance between the electrodes.

According to another aspect of the invention, a method is provided for detecting gas bubbles in blood during a hemodialysis treatment of a patient. The method includes providing a plate having at least two aligned electrodes embedded within the plate, locating the plate over a microchannel such that the at least two aligned electrodes are located along a length of the microchannel in a flow direction through the microchannel, flowing blood through the microchannel in the flow direction, measuring an impedance between the electrodes, and determining a percentage of gas in the blood flowing through the microchannel based on the measured impedance between the electrodes.

According to another aspect of the invention, an apparatus is provided for detection of gas bubbles in blood during a hemodialysis treatment of a patient, wherein the hemodialysis treatment includes flowing the blood through a microchannel. The apparatus includes a plate and at least two aligned electrodes embedded within the plate. The plate is configured to be located over the microchannel such that the at least two aligned electrodes are located along a length of the microchannel in the flow direction. The apparatus further comprises means for measuring an impedance between the electrodes, and means for determining a percentage of gas in the blood flowing through the microchannel based on the measured impedance between the electrodes.

According to another aspect of the invention, a hemodialysis treatment apparatus includes a microchannel through which blood of a patient flows in a flow direction, a plate located over the microchannel, at least two aligned electrodes embedded within the plate wherein the at least two aligned electrodes are located along a length of the microchannel in the flow direction, means for measuring an impedance between the electrodes, and means for determining a percentage of gas in the blood flowing through the microchannel based on the measured impedance between the electrodes.

Technical effects of the methods and apparatuses described above preferably include the ability to detect gas bubbles in an array of closely spaced microchannels carrying a conductive fluid.

Other aspects and advantages of this invention will be better appreciated from the following detailed description.

DETAILED DESCRIPTION OF THE INVENTION

The present invention provides methods and void fraction sensors suitable for detection of gas bubbles in microchannels carrying a conductive fluid. According to an aspect of the invention, the sensors include two aligned electrodes placed along a length of a microchannel so as to be spaced apart in a flow direction through the microchannel. The percentage of any gas that may be present in a conductive fluid flowing through the microchannel is determined based on impedance measured between the electrodes.

Figure 2:
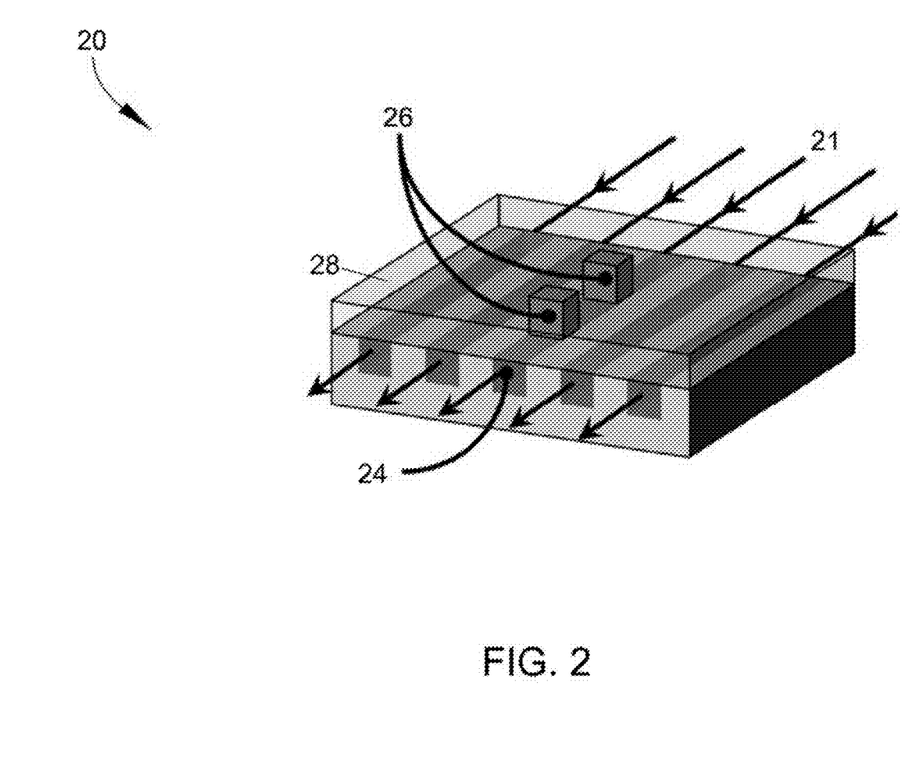
FIG. 2 schematically represents a nonlimiting electrical impedance-based sensor having a streamwise electrode pair configuration in accordance with certain aspects of the invention.

In order to monitor microchannel systems comprising an arrays of closely-spaced microchannels (for example, channels that are too closely spaced to locate a sensor therebetween, or channels separated by a dimension that is equal to or less than the width of the channels), FIG. 1 represents a sensor 20 comprising two aligned electrodes 26 embedded in a cover plate 28 (shown in phantom). The cover plate 28 is represented as located over a substrate in which multiple microchannels 24 have been formed by any suitable process. The cover plate 28 is positioned so that the electrodes 26 lie along the length of one of the microchannels 24 and therefore in a flow direction 21 through the microchannel 24. As such, the sensor 20 will be referred to herein as a "streamwise" sensor. The percentage of any gas that might be present within a conductive fluid flowing through the microchannel 24 is determined based on a measured impedance of the fluid between the electrodes 26. Such an arrangement provides for implementation in an array of closely spaced microchannels 24, for example, as represented in FIG. 2 wherein the distances between adjacent microchannels 24 are approximately equal to the cross-sectional widths of the microchannels 24. During investigations leading to the present invention, a sensor having a configuration similar to the sensor 20 was demonstrated to enable real-time flow regime control in small-scale (microscale) channels for the thermal regulation of electronic devices that generate large amounts of heat, and can be similarly applied for detection of gases in other fluidic microchannels.

Figure 3:
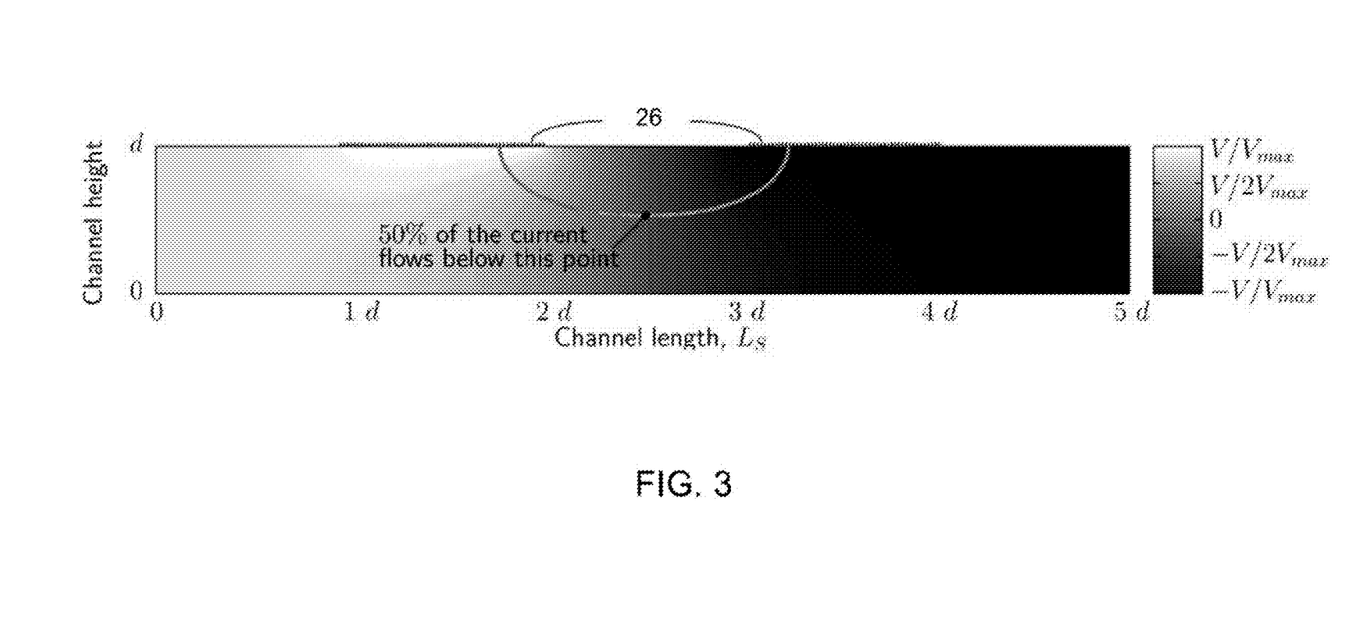
FIG. 3 represents a numerical simulation of the normalized potential field in water created using a streamwise impedance sensor.

Investigations leading to the present invention studied the structure and calibration of the streamwise sensor 20 depicted in FIG. 2 for use in microchannels having square cross-sections. The response of the sensor 20 was measured experimentally for electrodes 26 placed on top of one of the microchannels 24 in a streamwise configuration with a spacing distance of "d" between the electrodes 26 in the flow direction. To evaluate the sensor response, a numerical simulation was performed for a microchannel filled with water. For electrodes 26 separated by one electrode width, 50% of the current flowed across the cross-section below the mid-horizontal plane of the microchannel 24 in the region directly between the electrodes 26, as illustrated in FIG. 3. The electric field in the region between the electrodes 26 was thus well distributed for this geometric configuration, and was concluded to be suitable for detection of voids even in the lower part of the microchannel 24. Therefore, the impedance measurement may remain sensitive to void fraction for the predominant flow regimes within the flow microchannel 24.

Due to the inhomogeneous electric field distribution (a representative curved streamline is shown in FIG. 3), the streamwise configuration was not expected to yield a calibration curve for measurement of the instantaneous void fraction, i.e., the same void volume may result in different instantaneous impedance values based on the local values of the electric field. Instead, a calibration was obtained based on the time-averaged experimental impedance measurement versus time-averaged void fraction. This calibration was performed for the streamwise configuration at gas superficial velocities ranging between 0.17 m s$^{-1}$ and 13.7 m s$^{-1}$ and liquid superficial velocities ranging between 0.68 m s$^{-1}$ and 5.5 m s$^{-1}$.

Figure 4:
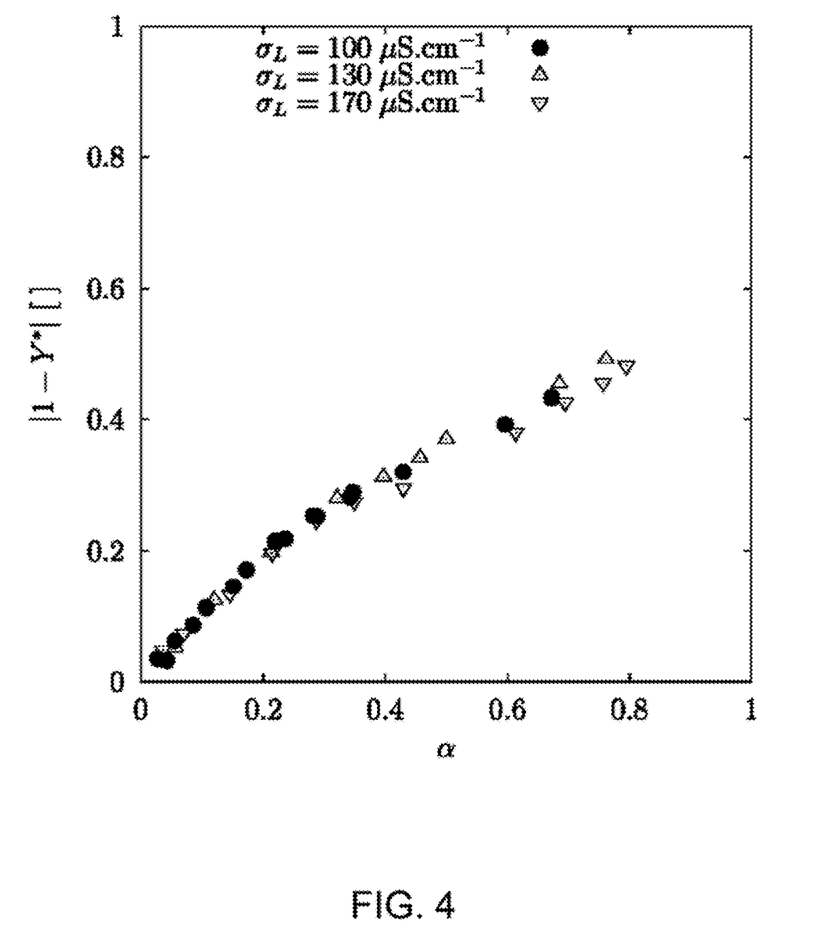
FIG. 4 represents a time-averaged dimensionless two-phase flow impedance (|1−Y*|) as a function of time-averaged void fraction for different water electrical conductivities (obtained for an electrode pitch of d and a sine wave exciter signal frequency of 20 kHz).

Such a calibration is shown to be independent of liquid-phase conductivity for the range shown in FIG. 4. The dimensionless impedance $Z/Z_0$ and the dimensionless admittance $1-Y^*$ may be expressed as:

$$\frac{Z}{Z_0} = Z\sigma_0 d$$

and $$1 - Y^* = \frac{Y - Y_0}{Y_1 - Y_0} = \frac{1/Z - 1/Z_0}{1/Z_1 - 1/Z_0}$$

where $Z_0$ and $Z_1$ are the theoretical expressions for full liquid and full gas impedance between electrodes, respectively, σ is the electrical conductivity, d is the distance between the electrodes, and Y is the admittance. The dimensionless impedance parameter $Z/Z_0$ only takes into account the liquid impedance properties, and is equivalent to 1/(1−α) regardless of the dielectric or resistive properties of the liquid under the assumption of stratified flow, where a is the void fraction. As a consequence, this number is appropriate when the overall impedance is dominated by the liquid impedance. As evident from FIG. 4, the continuity of the calibration curve was not affected by the flow regime, in contrast to what may be observed with the crosswise sensor configurations of the type represented in FIG. 1. These investigations demonstrated that it is possible to correlate the void fraction to the impedance using a streamwise electrode configuration.

Figure 5:
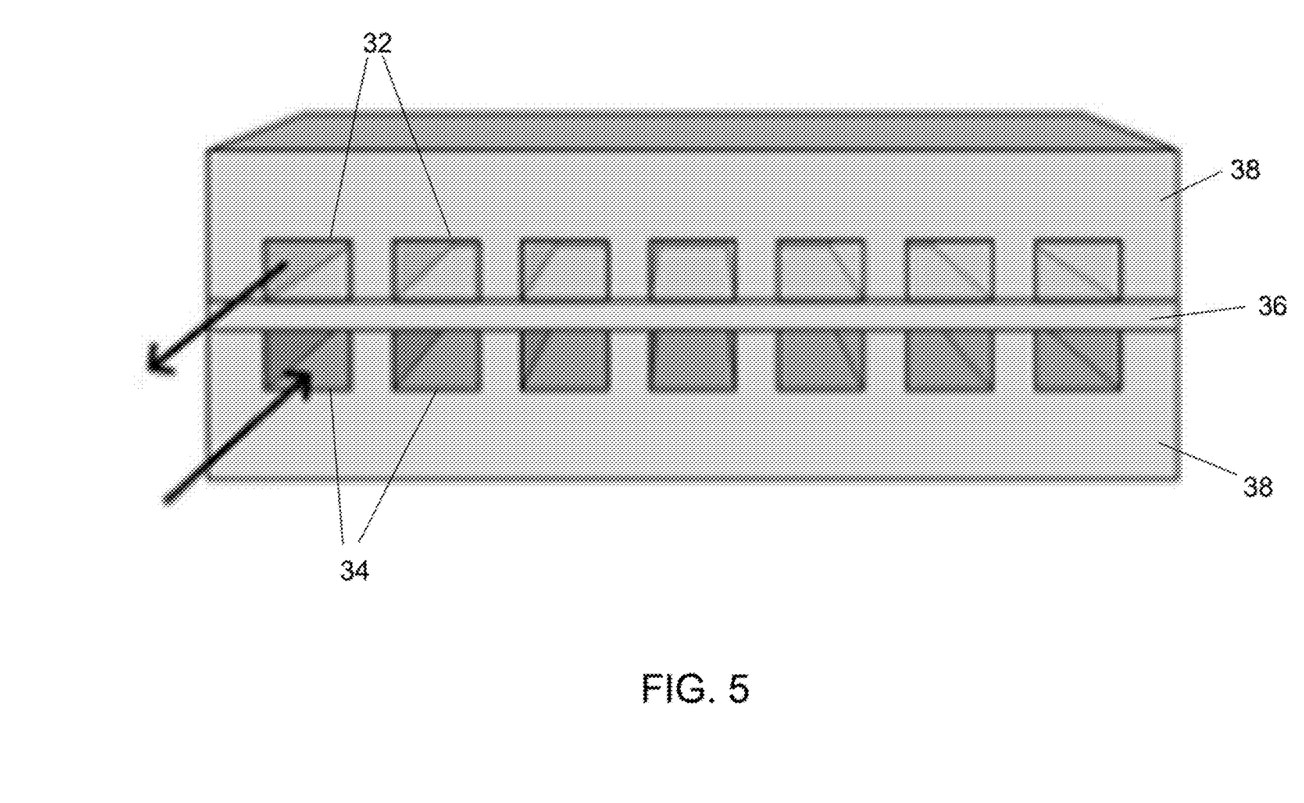
FIG. 5 schematically represents a cross-section of a microfluidic device for hemodialysis having an array of pairs of microchannels.

The methods and sensors described above may be applied to a hemodialysis treatment apparatus to detect gas bubbles in a patient's blood during a hemodialysis treatment. For example, a microfluidic device for hemodialysis may comprise an array of pairs of microchannels coated with a dielectric material, for example polyethylene oxide (PEO). Microchannels of each pair include openings that face each other and are separated by a membrane such that blood is able to flow through one of the microchannels while a dialysate flows in the opposite direction through the other microchannel. FIG. 5 schematically represents a nonlimiting example of a microfluidic device for hemodialysis having the aforementioned configuration, including microchannels 32 and 34 for dialysate and blood respectively, located within lamina 38 and separated by a membrane 36.

The sensors described herein may enable detection of gas bubbles in the PEO-coated (or otherwise rendered dielectric) microchannel array carrying a conductive fluid, common to medical applications. Output signals from the electrical sensor can be used to monitor the fluid flow in the small-scale microchannel. The orientation of the streamwise electrodes 26 provides the ability to incorporate a plurality of sensors 20 in an array of very small microchannels, which is believed to not be possible using other conventional and existing electrical-sensing-based methods.

In view of the above, the sensor time resolution and electrical output can be used to monitor the fluid flow in the microchannel. The streamwise configuration is particularly adaptable to the microscale geometry and can be more readily manufactured than crosswise electrode geometries such as the configuration represented in FIG. 1. In addition, the ability to apply the streamwise sensor 20 to an array of microchannels allows for the application of the streamwise sensors in microchannel-based hemodialysis treatments apparatuses.

While the invention has been described in terms of specific embodiments, it is apparent that other forms could be adopted by one skilled in the art. For example, the physical configuration of the sensor could differ from that shown, and materials and processes/methods other than those noted could be used. Therefore, the scope of the invention is to be limited only by the following claims.

The invention claimed is:

1. An apparatus for detection of gas bubbles in a microchannel formed in a substrate, the microchannel having a conductive fluid flowing therethrough in a flow direction, the apparatus comprising:
    a plate;
    at least two aligned electrodes embedded within the plate, wherein the plate is configured to be located over the microchannel such that the at least two aligned electrodes are located along a length of the microchannel in the flow direction;
    means for measuring an impedance between the electrodes; and
    means for determining a percentage of gas in the conductive fluid flowing through the microchannel based on the measured impedance between the electrodes;
    wherein the substrate is a component of a microfluidic device for hemodialysis, the microchannel is one of an array of closely spaced pairs of microchannels formed in the substrate, and each pair of microchannels includes openings that face each other and are separated by a membrane such that blood flows through a first microchannel of the pair of microchannels while a dialysate flows in an opposite direction through a second microchannel of the pair of microchannels.

2. The apparatus of claim 1, wherein the plate has a plurality of pairs of aligned electrodes embedded therein and being configured to be located over the array of closely spaced pairs of microchannels such that each of the pairs of aligned electrodes embedded in the plate are located along a length of a respective one of the array of closely spaced pairs of microchannels in the flow direction thereof, the conductive fluid flowing through the array of closely spaced pairs of microchannels in the flow direction.

3. A method for detecting gas bubbles in a microchannel formed in a substrate, the microchannel having a conductive fluid flowing therethrough in a flow direction, the method comprising:
    providing a plate having at least two aligned electrodes embedded within the plate;
    locating the plate over the microchannel such that the at least two aligned electrodes are located along a length of the microchannel in the flow direction;
    measuring an impedance between the electrodes; and
    determining a percentage of gas in the conductive fluid flowing through the microchannel based on the measured impedance between the electrodes;
    wherein the substrate is a component of a microfluidic device for hemodialysis, the microchannel is one of an array of closely spaced pairs of microchannels formed in the substrate, each pair of microchannels includes openings that face each other and are separated by a membrane, and the method further comprises flowing blood through a first microchannel of the pair of microchannels and flowing a dialysate in an opposite direction through a second microchannel of the pair of microchannels.

4. The method of claim 3, wherein the plate has a plurality of pairs of aligned electrodes embedded therein, the method further comprising locating the plate over the array of closely spaced pairs of microchannels such that each of the pairs of aligned electrodes embedded in the plate are located along a length of a respective one of the array of closely spaced pairs of microchannels in the flow direction thereof, the conductive fluid flowing through the array of closely spaced pairs of microchannels in the flow direction.

5. The method of claim 3, wherein the method is a hemodialysis treatment of a patient that includes flowing blood through the microchannel.

6. A method of detecting gas bubbles in blood during a hemodialysis treatment of a patient, wherein the hemodialysis treatment includes flowing blood through a microchannel in a flow direction thereof, the method comprising:
    providing a plate having at least two aligned electrodes embedded within the plate;
    locating the plate over the microchannel such that the at least two aligned electrodes are located along a length of the microchannel in the flow direction;
    measuring an impedance between the electrodes; and determining a percentage of gas in the blood flowing through the microchannel based on the measured impedance between the electrodes;

wherein the microchannel is one of an array of closely spaced pairs of microchannels formed in a substrate, each pair of microchannels includes openings that face each other and are separated by a membrane, and the method further comprises flowing blood through a first microchannel of the pair of microchannels and flowing a dialysate in an opposite direction through a second microchannel of the pair of microchannels.

7. The method of claim 6, wherein the plate has a plurality of pairs of aligned electrodes embedded therein, the method further comprising locating the plate over the array of closely spaced pairs of microchannels such that each of the pairs of aligned electrodes embedded in the plate are located along a length of a respective one of the array of closely spaced pairs of microchannels in the flow direction thereof, the blood flowing through the array of closely spaced pairs of microchannels in the flow direction.

8. An apparatus for detection of gas bubbles in blood during a hemodialysis treatment of a patient, wherein the hemodialysis treatment includes flowing blood through a microchannel in a flow direction thereof, the apparatus comprising:

a plate;

at least two aligned electrodes embedded within the plate, wherein the plate is configured to be located over the microchannel such that the at least two aligned electrodes are located along a length of the microchannel in the flow direction;

means for measuring an impedance between the electrodes; and means for determining a percentage of gas in the conductive fluid flowing through the microchannel based on the measured impedance between the electrodes;

wherein the microchannel is a first microchannel adjacent a second microchannel, each of the first and second microchannels includes openings that face each other and are separated by a membrane, the blood flows through the first microchannel in the flow direction, and a dialysate flows in an opposite direction through the second microchannel.

9. The apparatus of claim 8, wherein the first and second microchannels are in an array of closely spaced microchannels formed in a substrate, the plate has a plurality of pairs of aligned electrodes embedded therein and being configured to be located over the array of closely spaced microchannels such that each of the pairs of aligned electrodes embedded in the plate are located along a length of a respective one of the array of closely spaced microchannels in the flow direction thereof, the blood flowing through the array of closely spaced microchannels in the flow direction.

10. A hemodialysis treatment apparatus comprising:

a microchannel through which blood of a patient flows in a flow direction;

a plate located over the microchannel;

at least two aligned electrodes embedded within the plate, the at least two aligned electrodes being located along a length of the microchannel in the flow direction;

means for measuring an impedance between the electrodes; and means for determining a percentage of gas in the conductive fluid flowing through the microchannel based on the measured impedance between the electrodes;

wherein the microchannel is a first microchannel adjacent a second microchannel, each of the first and second microchannels includes openings that face each other and are separated by a membrane, the blood flows through the first microchannel in the flow direction, and a dialysate flows in an opposite direction through the second microchannel.

11. The apparatus of claim 10, wherein the first and second microchannels are in an array of closely spaced microchannels formed in a substrate, the plate has a plurality of pairs of aligned electrodes embedded therein and being located over the array of closely spaced microchannels such that each of the pairs of aligned electrodes embedded in the plate are located along a length of a respective one of the array of closely spaced microchannels in the flow direction thereof, the blood flowing through the array of closely spaced microchannels in the flow direction.

* * * * *